United States Patent [19]

Monticelli et al.

[11] 4,118,621

[45] Oct. 3, 1978

[54] PHOTO ELECTRIC BIASED PHOTO DIODE OPERATIONAL AMPLIFIER

[75] Inventors: Dennis M. Monticelli, Fremont; Robert S. Sleeth, San Jose, both of Calif.

[73] Assignee: National Semiconductor Corporation, Santa Clara, Calif.

[21] Appl. No.: 798,728

[22] Filed: May 19, 1977

[30] Foreign Application Priority Data

Feb. 9, 1977 [DE] Fed. Rep. of Germany ....... 2705308

[51] Int. Cl.² .............................................. H01J 39/12
[52] U.S. Cl. .............................. 250/214 A; 250/214 C; 330/59; 330/288; 330/308
[58] Field of Search ........... 250/214 A, 214 P, 214 C; 330/59, 257, 288, 308; 354/31

[56] References Cited

U.S. PATENT DOCUMENTS

| 3,424,908 | 1/1969 | Sitter | 250/214 A |
| 3,850,809 | 11/1974 | Mannonen | 250/214 A |

Primary Examiner—Lawrence J. Dahl
Attorney, Agent, or Firm—Gail W. Woodward

[57] ABSTRACT

A circuit useful in replicating the current produced in a photo diode operated as a current source at zero bias. A second scaled area photo diode is used to bias the circuit to maintain the zero bias over a wide range of illumination levels. The circuit operates in the picoampere range and is linear over at least six orders of magnitude.

10 Claims, 2 Drawing Figures

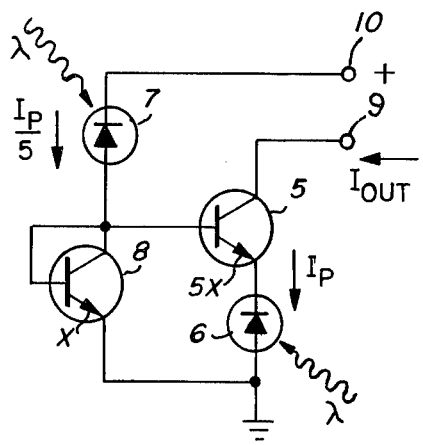
Fig_1
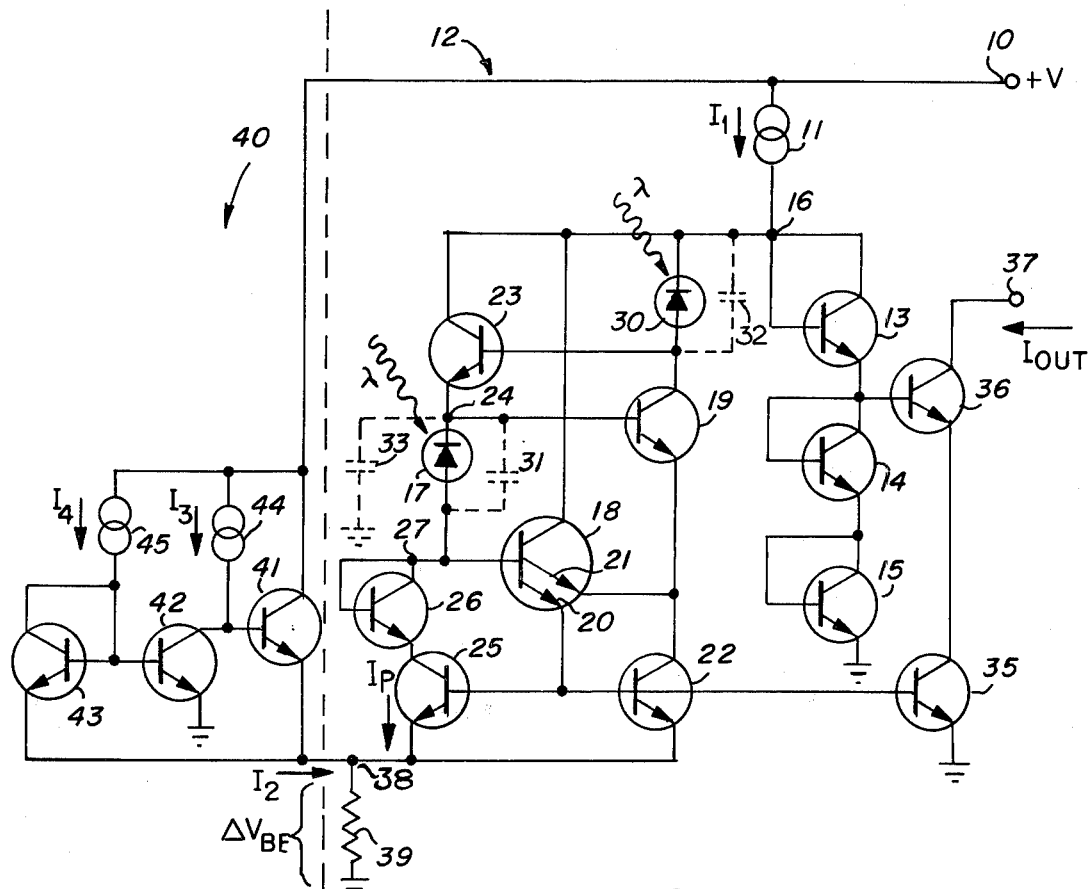
Fig_2

PHOTO ELECTRIC BIASED PHOTO DIODE OPERATIONAL AMPLIFIER

BACKGROUND OF THE INVENTION

Silicon photo diodes have excellent inherent linearity of current response to illumination. In addition, their rapid response, wavelength suitability and capability of being integrated into bipolar silicon integrated circuits have lead to their widespread use in automatic camera control circuits. This application imposes severe requirements on the photo diode. The illumination, which ranges from full sunlight to moonlight (or even less), involves about six orders of magnitude. Accordingly, if the bright response involves microampere currents, the low levels produce picoampere currents. This value is so small as to be masked by silicon junction leakage currents. It is also desirable that the response be rapid enough to respond to widely used flash illumination devices.

One solution to the leakage problem is to increase photo diode area. However, any increase in junction area increases perimeter which adversely affects leakage. In addition, large junction areas increase capacitance and thus can adversely affect associated circuit response time. Furthermore, such an approach results in increasing integrated circuit chip area. A more appropriate solution has been to operate the photo diode in a circuit that produces zero bias across the diode terminals. This greatly reduces leakage current and extends the linear response range. By using suitable circuitry, the response time can be made suitably small. However, it is difficult to devise a circuit that maintains zero bias in a manufacturable integrated circuit that meets all of the other performance requirements.

SUMMARY OF THE INVENTION

It is an object of the invention to use scaled photo diodes in a circuit that responds linearly to illumination and holds the bias across at least the larger of the photo diodes to zero.

It is a further object of the invention to integrate a pair of photo diodes into a silicon integrated circuit that is adaptively biased by one photo diode and maintains the other photo diode at zero bias.

It is a feature of the invention that integrated circuit area controls can be used to fabricate a light responsive circuit in which one photo diode adaptively biases the circuit and the second photo diode is operated at zero bias.

It is a further feature of the invention that a low-voltage, low-current, adaptively-biased integrated circuit using scaled photo diodes can be made to have extended light sensing range and speed of response.

These and other objects and features are achieved in an integrated circuit (IC) characterized as follows. A pair of scaled area photo diodes are fabricated into the IC that includes a biopolar transistor circuit that produces a linear output current as a function of illumination. One photo diode is connected to adaptively bias the circuit and the other photo diode, the larger of the two, is caused to operate at zero bias. The zero bias is achieved by connecting the photo diodes to transistors that have their areas scaled in the same ratio. If the transistors are connected into a circuit that produces equal current density in a pair of transistors and a photo diode is coupled in series with the emitter of one of the pair of transistors, it will operate at zero bias.

BRIEF DESCRIPTION OF THE DRAWING

FIG. 1 is a schematic diagram of a simplified circuit employing the invention; and FIG. 2 is a schematic diagram of an integrated light to current converter employing the invention.

DESCRIPTION OF THE INVENTION

In the following circuit description, it is assumed that the transistor involved have Beta (current gain factors) of in the range of 100 to 200. This is reasonable for state of the art IC fabrication processes using NPN transistors. This means that typical base currents are 1% or less of the collector current. To a first approximation the base currents can be neglected in circuit analysis.

FIG. 1 is a simplified schematic diagram of a circuit illustrating the invention. A transistor 5 has an input or main photo diode 6 coupled to its emitter. A biasing photodiode 7 is coupled between the base of transistor 5 and the supply potential at 10 referenced to ground. A diode connected transistor 8 is coupled from the base of transistor 5 to ground and acts to set the base potential at $V_{BE}$ above ground when conduction is produced. This ensures that the potential across photo diode 6 is zero even when it is supplying current. The emitter of transistor 5 is made larger than that of transistor 8 with a ratio of 5 being indicated. Biasing photo diode 7 is made to have one fifth of the area of photo diode 6. This ratioing ensures that the current densities in transistors 5 and 8 are the same, thus forcing the potential across photo diode 6 to zero.

The ratioing shown is selected as a convenient value. The higher the ratio the greater the economy of space utilization in IC fabrication. The ratio must not exceed the lowest current gain or Beta to be encountered in transistor 5. To be economical the ratio should exceed 2. Ordinarily a ratio of 10 would be considered as near to optimum, the value of 5 being an easily achieved conservative ratio.

In operation both photo diodes 6 and 7 are exposed to the same light input. As a practical matter they will be manufactured in adjacent or closely spaced areas on an integrated circuit fabricated into a silicon substrate along with the associated circuitry. The smaller photo diode 7 will act to bias transistor 5. Photo diode 6 supplies the main photo current $I_p$. $I_p$ will appear at terminal 9 as $I_{OUT}$ for supplying a load device (not shown). This uncommitted collector output is preferred and the transistor acts as a current sink for any suitable load. Other output circuitry can be used as desired.

The circuit responds linearly to light input and forces zero potential across photo diode 6. There will be little or no leakage current in the large or main photo diode even at the lowest light (and hence current) level. While a small leakage current may flow in photo diode 7, it will produce very little current flow in photo diode 6. Most of this current flows in diode 8 and will produce only a very small potential rise at the base of transistor 5. Since photo diode 6 will, due to its very low conductivity, present a very high resistance to the emitter of transistor 5, leakage in photo diode 7 will produce only a small increase in reverse bias across photo diode 6. This will prevent any flow of collector current. Thus at very low light levels the $I_{OUT}$ will be extremely low and controlled by the current in photo diode 6 which, due to its nearly zero operating bias, generates practically no leakage current.

The schematic diagram of FIG. 2 shows a complete circuit including a large area photo diode, a smaller biasing photo diode, and means to replicate the photo current in an output circuit. The term replicate as used herein means to produce an output that is in the form of a multiple of the actual photo current. The multiple can be unity or some other ratio established by circuit design as will be shown hereinafter. Thus a photo diode producing microamperes can have its output replicated to produce milliamperes without resorting to additional amplifiers. Yet the output is related to the photocurrent by a constant over many orders of magnitude variation in current.

In the circuit shown, a positive supply potential is applied to terminal 10 with respect to ground. A current source 11 establishes the drain $I_1$ of photosensitive section 12 on the right hand side of the dashed line. Typically $I_1$ will be on the order of 200 microamperes. At low light levels $I_1$ established through source 11 flows largely through diode connected transistors 13–15. Thus the voltage of node 16 will be at $3V_{BE}$ or about 2.1 volts at 300° K.

Photo diode 17 is a silicon junction device having a substantial area selected to provide the desired photocurrent range. By using a silicon junction for this application and employing a suitably shallow junction depth, very efficient optical conversion is obtained and such devices are quite linear over the light intensity range of full sunlight to moonlight (about 6 orders of magnitude). Typically the photo current, $I_p$, will be about 10 microamperes in sunlight illumination and about 10 picoamperes for a dimly lit scene.

Photo diode 17 is connected across the input terminals of a differential amplifier composed of transistors 18 and 19. The emitter of transistor 19 and emitter 21 of double emitter transistor 18 are connected together to the collector of transistor 22 which acts as a light dependent current source. Emitter 20 of transistor 18 is coupled to the base of transistor 22 to establish the differential amplifier tail current. Emitter follower connected transistor 23 couples the output of the differential amplifier back to its inverting input at node 24. Thus node 24 will follow $1V_{BE}$ below the potential at the collector of transistor 19. This produces a local negative feedback loop around the differential amplifier that will act to stabilize its operating point.

Emitter 20 of transistor 18 is also coupled to the base of transistor 25, the collector of which is coupled to the differential amplifier noninverting input, at node 27, through diode connected transistor 26. Since this loop includes an inversion, it too will produce negative feedback and act to balance the current distribution in the differential amplifier.

Photo diode 30, which is coupled in series with the collector of transistor 19, biases the differential amplifier and sets its operating point. The illumination of photo diode 30 establishes a photo current which, by virtue of the negative feedback loop, including transistor 23, flows in the collector of transistor 19. The same illumination establishes a current in photo diode 17 which, due to the negative feedback loop including transistor 25, will flow in the collector of transistor 25.

The area of photo diode 30 is made small compared with that of photo diode 17. The area of the emitter of transistor 19 is made the same as that of emitter 21 in transistor 18 and the emitter of transistor 22. The emitter of transistor 25 is made larger than the others by a ratio that will accommodate the photo diode ratio. If the photo diode area ratio is 5 to 1, the emitter of transistor 25 is made 2½ times larger than the others. This ratio is established because transistor 22 carries the combined currents of emitter 21 and the emitter of transistor 19. Thus transistor 22 operates at double the current density. Making the emitter of transistor 25 2½ times that of transistor 22 gives it a 5 to 1 ratio with respect to transistor 19. Thus the current densities of the emitters of transistors 19 and 25 are the same. This arrangement ensures that the potential difference between nodes 24 and 27 will be substantially zero as determined by simple device area ratios. Such area control is achieved with suitable precision using coventional integrated circuit fabrication techniques. The current labeled, $I_p$, is equal to the photo current of photo diode 17.

From the above, it can be seen that photo diode 17 is operated at substantially zero bias and thereby has very little leakage so that it will be linearly operative in the picoampere range. Photo diode 30 is also operated near zero bias in the circuit shown. Node 16, which is $3V_{BE}$ above ground, is connected to one side of photo diode 30. The other side of photo diode 30 couples through $V_{BE}$ of transistors 23 and 19 to emitter 21. Emitter 20 is the $V_{BE}$ of transistor 35 above ground. Thus, to a first approximation, both ends of photo diode are at $3V_{BE}$ above ground and leakage is kept very low.

Since the base of transistor 35 is also coupled to the bases of transistors 22 and 25, its collector current will be a function of $I_p$. However, the emitter of transistor 35 is made twice as large as that of transistor 25 and is returned to ground. The emitters of transistors 22 and 25 are both returned to a small positive potential at node 38 called $\Delta V_{BE}$. This potential is produced by circuit portion 40 which will be described hereinafter. The action of $\Delta V_{BE}$ is to cause transistor 35 to operate at a multiple of $I_p$. For example, a $\Delta V_{BE}$ (using the above expressed emitter area ratio) of 120 millivolts will produce an output current of 200 times $I_p$.

The collector current in transistor 35 is buffered by transistor 36 to produce $I_{OUT}$ at terminal 37. This uncommitted collector can sink 2 ma for an $I_p$ of 10 microamperes. This form of buffering reduces the effect of output terminal loading reflecting Miller capacitance loading on the bases of transistors 22 and 25.

Photo diodes of the p-n junction variety are of relatively large area and, since they operate at zero bias, have substantial capacitance. The stray capacitances are shown in dashed connection in the schematic. Element 31 is the junction capacitance of the larger photo diode 17. This capacitance acts to compensate the differential amplifier in that it reduces gain at high frequencies through shunting of the differential input. It provides the dominant pole of the circuit and sets the response of the loop, including transistors 18, 25, and 26. Capacitance 32 is the junction capacitance of the smaller photo diode 30. This capacitance compensates the feedback loop defined by transistors 19 and 23 to improve overall transient performance. Capacitance 33 is the epitaxial to substrate junction capacitance associated with integrated circuit construction. This element is parasitic but, since it appears at a low impedance circuit node (the emitter of an emitter follower 23), its effect will be minimized. From the above, it can be seen that the circuit either minimizes the effects of unavoidable capacitances or uses them to compensate performance.

In order to more fully understand the circuit, the startup transient under illumination will now be described. This is an important consideration because in one important application, the automatic camera, the circuit is normally off and is energized as the camera shutter is operated.

As +V is applied, source 11 rapidly pulls node 16 to its regulated level of $3V_{BE}$. This rise is coupled through capacitance 32 to the base of transistor 23 which turns on and pulls node 24 up. Photo diode 30 photo current also acts to pull the base of transistor 23 up. This enables transistor 19 while capacitance 31 and photo diode 17 couple the rise to the base of transistor 18. Transistor 18, by way of emitter 20, pulls the bases of transistors 25, 22, and 35 up which completes the conductive circuit. Thus the circuit is self starting and compensated to start rapidly. Typical embodiments of the circuit display startup times of less than 100 microseconds at the higher light levels. The response to a step function of illumination is about 5 microseconds at the higher peak light values.

As pointed out above, $\Delta V_{BE}$ at node 38 is employed to ratio and replicate $I_p$ at $I_{OUT}$ at some multiple of $I_p$. If a fixed voltage were to be employed, the ratioing would be a function of temperature. The circuit portion 40 is arranged to provide a $\Delta V_{BE}$ that varies with temperature to keep the ratioing constant or independent of temperature or supply variations.

Transistor 41 is coupled between +V and node 38 and passes a current that will be determined by the biasing imposed by the other components. Transistor 42 is coupled between the base of transistor 41 and ground. A current source 44 supplies $I_3$ as collector current of transistor 42. Diode connected transistor 43 is coupled between the base of transistor 42 and node 38. Current source 45 supplies $I_4$ to diode 43. It can be seen that the emitter of transistor 41 is coupled through diode 43 to the base of transistor 42. Transistor 42, operating as a high gain common emitter amplifier, is collector coupled to the base of transistor 41. Thus, a high gain feedback loop is present and having one inversion produces negative feedback. Thus, the circuit acts to stabilize the potential at node 38. The value of $\Delta V_{BE}$ at node 38 due to circuit 40 is:

$$\Delta V_{BE} = (KT/Q 1_n) (I_3 A_{43}/I_4 A_{42}) \qquad (1)$$

where:

$K$ = Boltzman's constant
$T$ = Absolute temperature
$Q$ = Electron charge
$A_{42}$ = Emitter area of transistor 42
$A_{43}$ = Emitter area of transistor 43.

In a typical example where $I_3$ is ten times $I_4$ and transistor 43 is 10 times the size of transistor 42, $\Delta V_{BE}$ will be about 120 millivolts at 300° K.

The total current flowing through resistor 39 will be established by the value of the resistor. In practice, $I_2$ is made several times larger than $I_p$. For example, if the maximum $I_p$ is to be 10 microamperes, $I_2$ could be made 40 microamperes. For the above noted 120 millivolts, resistor 39 would be 2.4K ohms.

The adaptively biased light to current converter has been described using two photo detectors. In principle still more photo diodes could be used and other circuit configurations employed without departing from the spirit and intent of the invention. Accordingly, it is intended that the invention be limited only by the following claims.

We claim:

1. A circuit for replicating the photo current of an illumination responsive element which generates a photo current when exposed to illumination, said circuit comprising:
   a first photo diode adapted for exposure to said illumination to generate a current proportional to said illumination;
   amplifying means coupled to said first photo diode, said amplifying means including means to force the potential across said first photo diode to substantially zero volts thereby to provide linearity between said illumination and said photo current; and
   means for biasing said amplifying means substantially in proportion to said illumination, said means for biasing including a second photo diode adapted for exposure to said illumination and coupled to said amplifying means to provide illumination dependent bias thereto.

2. The circuit of claim 1 wherein said second photo diode has a light responsive area that is a fraction of that of said first photo diode to provide a ratio therebetween and is otherwise constructed like said first photo diode.

3. The circuit of claim 1 wherein said amplifying means includes a bipolar transistor, said first photo diode is coupled in series with the emitter electrode of said bipolar transistor, and said second photo diode is coupled to provide base current to said bipolar transistor.

4. The circuit of claim 3 further including a shunt diode coupled to said bipolar transistor to shunt a portion of the current developed by said second photo diode away from the base of said bipolar transistor.

5. The circuit of claim 4 wherein said shunt diode has an anode area smaller than the collector area of said bipolar transistor by a ratio equal to said ratio between said first and said second photo diodes.

6. The circuit of claim 4 wherein said ratios are selected to be smaller than the base to emitter current gain of said bipolar transistor.

7. The circuit of claim 2 wherein said amplifying means includes a differential amplifier having inverting and noninverting input terminals and an output terminal, means for coupling said first photo diode between said input terminals, first feedback means for coupling said output terminal to said inverting input terminal to stabilize said differential amplifier and means for coupling said second photo diode to said feedback means whereby said second photo diode establishes the current flowing in said differential amplifier.

8. The circuit of claim 7 wherein said differential amplifier is coupled to means including a second feedback means to control the current flowing in said differential amplifier and replicate the current in said first photo diode.

9. The circuit of claim 8 wherein said second feedback means has a current control characteristic that accomodates equal current densities in said first and said second photo diodes.

10. The circuit of claim 8 including means for operating said circuit from a constant voltage supply the value of said voltage being selected to operate said second photo diode at approximately zero potential.

* * * * *